United States Patent [19]

Siren

[11] Patent Number: 5,654,280

[45] Date of Patent: Aug. 5, 1997

[54] PHARMACEUTICAL COMPOSITION

[75] Inventor: Matti Siren, Helsinki, Finland

[73] Assignee: Perstorp AB, Perstorp, Sweden

[21] Appl. No.: 373,793

[22] Filed: Jan. 17, 1995

Related U.S. Application Data

[63] Continuation-in-part of Ser. No. 88,511, Jul. 6, 1993, abandoned, which is a continuation-in-part of Ser. No. 862,563, Dec. 18, 1990, abandoned.

[30] Foreign Application Priority Data

Dec. 21, 1989 [SE] Sweden ................... 8904354

[51] Int. Cl.$^6$ .................. A61K 31/70; C07H 11/04; C07H 13/00
[52] U.S. Cl. ........................... 514/23; 536/117
[58] Field of Search ................. 514/23; 536/117

[56] References Cited

U.S. PATENT DOCUMENTS

| | | | |
|---|---|---|---|
| 3,408,257 | 10/1968 | Kawamori et al. | 536/117 |
| 3,931,402 | 1/1976 | Ghielmetti et al. | 424/180 |
| 4,444,780 | 4/1984 | Capetola et al. | 424/267 |
| 4,448,771 | 5/1984 | Cattani et al. | 424/180 |
| 4,745,185 | 5/1988 | Maryanoff et al. | 536/117 |
| 4,793,945 | 12/1988 | Siren | 514/103 |
| 4,968,790 | 11/1990 | DeVries et al. | 536/117 |
| 5,015,634 | 5/1991 | Siren | 514/103 |

FOREIGN PATENT DOCUMENTS

| | | |
|---|---|---|
| 6065M | 11/1966 | France . |
| 1158456 | 7/1969 | France . |
| 7346M | 11/1969 | France . |
| 2529459 | 1/1984 | France . |
| 2508474 | 9/1976 | Germany . |
| 2629845 | 1/1978 | Germany . |
| 3109202 | 4/1982 | Germany . |
| 1092200 | 11/1967 | United Kingdom ........... 536/117 |

OTHER PUBLICATIONS

Tener et al, "Phosphorylated Sugars. VI. Syntheses of α-D-Ribofuranose 1,5-Diphosphate and α-D-Ribofuranose 1-Pyrophosphate 5-Phosphate" published 1958, pp. 1999-2004.

PCT/SE90/000843, International Search Report, Perstorp AB et al. 4 pages.

Primary Examiner—John Kight
Assistant Examiner—Everett White
Attorney, Agent, or Firm—Scully, Scott, Murphy & Presser

[57] ABSTRACT

A pharmaceutical composition comprising a pharmaceutically active ingredient selected from the group consisting of trisphosphorylated pentoses, pentitols or anhydropentitols, trisphosphorylated hexoses, hexitols or anhydrohexitols and trisphosphorylated heptoses, heptitols or anhydroheptitols. The active ingredient can also be present in the form of a salt. The invention also includes a method of preventing or alleviating tissue damage in mammals, including man. The method comprises administering an effective amount of the pharmaceutical composition.

19 Claims, No Drawings

PHARMACEUTICAL COMPOSITION

This is a continuation-in-part of U.S. patent application, Ser. No. 088,511 filed on Jul. 6, 1993, now abandoned which is a continuation-in-part of U.S. patent application, Ser. No. 862,563 filed Dec. 18, 1990, now abandoned.

FIELD OF THE INVENTION

The present invention relates to a pharmaceutical composition comprising a pharmaceutically active ingredient comprising a trisphosphorylated sugar compound having five, six or seven carbon atoms. In particular, the present invention describes a pharmaceutical composition comprising a pharmaceutically active ingredient selected from the group consisting of trisphosphorylated pentoses, pentitols or anhydropentitols, trisphosphorylated hexoses, hexitols or anhydrohexitols and trisphosphorylated heptoses, heptitols or anhydroheptitols. The invention further relates to a method of preventing or alleviating tissue damage in mammals including man comprising administering an effective amount of said pharmaceutical composition.

BACKGROUND OF THE INVENTION

Many existing diseases and conditions are not being treated in a correct way. The underlying causes of various diseases are barely understood and in many cases only the symptoms of the disease can be treated by existing drugs, without any reversal of the disease per se. This is especially true for such conditions as tissue damage, diabetic complications, cardiovascular diseases, etc. According to the present invention it has quite unexpectedly been found possible to treat conditions and diseases belonging to the above described group using a pharmaceutical composition described by the present invention.

SUMMARY OF THE INVENTION

The present invention describes a pharmaceutical composition comprising a pharmaceutically active ingredient or salt thereof which is useful for treating or preventing tissue damage. The active ingredient is selected from the group consisting of trisphosphorylated pentoses, trisphosphorylated pentitols or corresponding anhydropentitols, trisphosphorylated hexoses, trisphosphorylated hexitols or corresponding anhydrohexitols, trisphosphorylated heptoses and trisphosphorylated heptitols or corresponding anhydroheptitols.

In addition to the phosphorylated compound, the present composition comprises at least one pharmaceutically acceptable carrier, excipient or additive. Said phosphorylated compound can also be used in the form of a pharmaceutically acceptable salt, such as, for example, an ammonium salt or a salt of sodium, potassium, calcium, zinc or magnesium or a mixture thereof. In addition, the typical pharmaceutically acceptable salts may also be utilized in the pharmaceutical composition of the present invention. Thus, a combination of the compound in acid and salt form is within the scope of the invention.

DETAILED DESCRIPTION OF THE INVENTION

The present invention is directed to a pharmaceutical composition comprising a pharmaceutically active ingredient comprising a trisphosphorylated sugar compound having five, six or seven carbon atoms. In particular, the present invention describes a pharmaceutical composition comprising a pharmaceutically active ingredient selected from the group consisting of trisphosphorylated pentoses, pentitols, or anhydropentitols, trisphosphorylated hexoses, hexitols or anhydrohexitols and trisphosphorylated heptoses, heptitols or anhydroheptitols. The invention further relates to a method of preventing or alleviating tissue damage in meals including man comprising administering an effective amount of said pharmaceutical composition.

Monosaccharides are aliphatic polyhydroxyaldehydes or polyhydroxyketones or derivatives thereof. They are designated as aldoses and ketoses with the prefix "aldo" and "keto" respectively, such as, for example, aldohexoses and ketohexoses. The various aldoses and ketoses containing 5, 6, and 7 ring carbon atoms are known compounds. Examples include ribose, arabinose, xylose, lyxose, allose, altrose, glucose, mannose, gulose, idose, galactose, talose, ribulose, xylulose, psicose, fructose, sorbose, tagatose, and the like. These aldoses may exist in various stereochemical forms. For example, for sugars with more than one asymmetric carbon, the symbols $\underline{D}$ and $\underline{L}$ refer to the absolute configuration of the asymmetric carbon furthest from the aldehyde or keto group. The preferred sugars are in the $\underline{D}$ configuration, although all of the various stereoisomers as well as racemic mixtures thereof can be used to make the triphosphorylated compounds of the present invention. These sugar compounds can be exemplified by the aldopentose D-arabinose, the ketopentose D-xylulose and the aldohexose D-glucose.

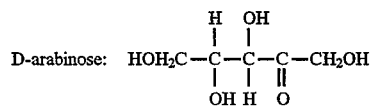

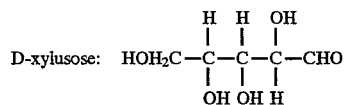

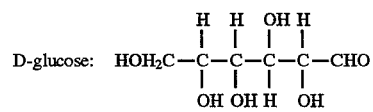

The optical isomer of D-arabinose, D-xylulose and D-glucose is L-arabinose, L-xylulose and L-glucose. Glucose is a preferred monosaccharide to be utilized to make the pharmaceutical compositions of the present invention partly because glucose is a frequent aldohexose and partly because glucose is representative for the properties of other monosaccharides. Glucose, like all monosaccharides, can exist in various configurations. D/L-glucose as an aldehyde only exists in solutions, but certain stable derivatives having the aldehyde structure are known.

The predominant form of pentoses and hexoses in solution are not open chains. Rather, the open chain forms of these sugar cyclize into rings. For example, using glucose as exemplary, D/L-glucose further exists as hemiacetals resulting from an intermolecular addition of one of the hydroxyl groups to the carbonyl group. Glucose normally forms a six membered ring, a so called pyranose ring, but also exists in the form of a five membered ring, a furanose ring, thus producing α- or β- glucopyranose and α- or β- glucofuranose.

α-glucopyranose:

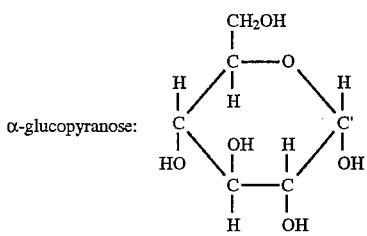

In glucopyranose, Carbon atoms 1 ($C^1$) is asymmetric. Therefore, two stereoisomers exist, depending on whether the hydroxyl group is situated on the α or β level. Both isomers crystallize as monohydrate or water-free.

β-glucofuranose:

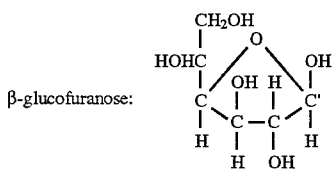

With respect to glucofuranose, Carbon atom 1 ($C^1$) is asymmetric and therefore two stereoisomers exist depending on whether the hydroxyl group is situated on the α or β level. Glucofuranose is unstable and exists only in solutions. Ethylglucosides thereof can be obtained as crystals, but also other crystalline derivatives exist.

Glycosides are derivatives wherein the hydroxy atom at carbon atom number 1 has been replaced with an ether group, such as alkyl group containing 1–10 carbon atoms, aryl group (aromatic group containing carbon and hydrogens containing 4n+2 ring carbon atoms, wherein n is 1, 2, 3, 4, and so on. Examples include phenyl, naphthyl and the like), arylalkyl containing 7–25 carbon atoms and the like. The simplest glucosides (glycosides containing glucose as the monosaccharide) are α- and β-methylglucoside.

Methyl -α-D-glucoside:

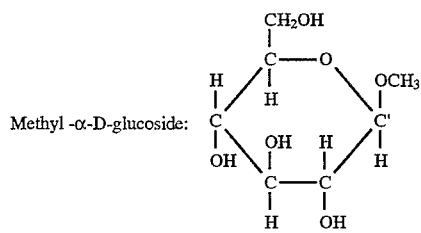

The aldoses and ketoses can be converted to other derivatives. For example, they can be converted to sugar alcohols, wherein the carboxyl group of monosaccharides are reduced to the alcohol (OH group). monosaccharides are reduced to the alcohol (OH group). The corresponding sugar alcohols of D-arabinose and D-glucose are D-arabinitol and D-glucitol (sorbitol). Reduction of aqueous solutions of the monosaccharide, such as $H_2$ gas in the presence of metal catalysts, or Na amalgam, produces the corresponding sugar alcohol.

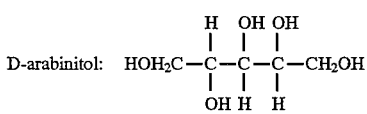

D-glucitol:

$$\text{HOH}_2\text{C}-\overset{\overset{\text{H}}{|}}{\text{C}}-\overset{\overset{\text{H}}{|}}{\underset{\underset{\text{OH}}{|}}{\text{C}}}-\overset{\overset{\text{OH}}{|}}{\underset{\underset{\text{OH}}{|}}{\text{C}}}-\overset{\overset{\text{H}}{|}}{\underset{\underset{\text{H}}{|}}{\text{C}}}-\overset{\overset{\text{H}}{|}}{\underset{\underset{\text{OH}}{|}}{\text{C}}}-\text{CH}_2\text{OH}$$

These reductions can also be carried out by enzymes.

Sugar alcohols, such as pentitols, hexitols and heptitols, can form internal ether bridges, produced through water splitting from two hydroxyl groups and pendant anhydro-ring formation. For example, arabinitol will be used to illustrate the formation of anhydrohexitols, however, the formation of anhydropenitols and anhydroheptitols are similar and formed by the loss of water. Arabinitol is drawn hereinbelow.

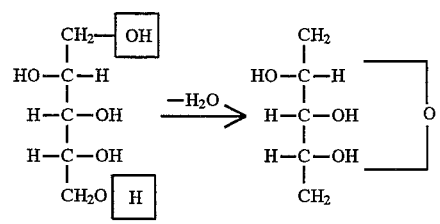

Loss of water in the boxes will provide the 1,5-anhydro-D-arabinitol. The ring structure is also depicted as follows:

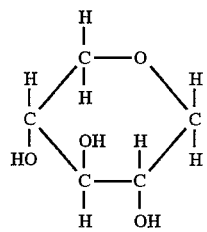

Sugar anhydrides exhibit chemical properties similar to those of glycosides.

The pharmaceutically active ingredient, according to the present invention, can be produced from the sugar, sugar alcohols or anhydro-sugar alcohols by known methods, such as phosphorylation. Thus, phosphorylation of the corresponding non-phosphorylated substance followed by a separation and purification will produce the active ingredient in the compositions of the present invention. Alternatively, in order to separate and purify the product, techniques based on the principle of ionic forces can be utilized. In order to obtain a sufficient phosphorylation, a mixture of orthophosphoric acid and polyphosphoric acid is preferably used. Also other phosphorylating agents can be used such as phosphorochloridates, e.g. diphenylchlorophosphate, cyanoethylphosphate, phosphoramidites such as N-arylphosphoramidates, wherein Ar is defined hereinabove (e.g. phenyl) and alkoxyalkylaminophosphines and the like. Inasmuch as the present invention is directed to the trisphosphorylated derivative, three hydroxy groups of the sugar, sugar alcohol and anhydrosugar alcohol are phophorylated in accordance with the present invention.

With respect to the phosphorylating agents, the organic moiety thereon is removed after the reaction is completed. For example, when using cyanoethylphosphate, the cyanoethyl group is removed with a diluting agent. When using diphenylchlorophosphate, the diphenyl group is removed with platinum oxide. Products obtained after the phosphorylation are separated by, for instance, an ion exchange column with a proper eluent, such as hydrochloric acid. As concentration is increased different fractions containing phosphorylated species with different degrees of substitution and different isomeric structures are separated. Precipitation with different cations is required in order to get pure salts of the compounds.

These various phosphylated compounds of the present invention exist in various stereoisomers such as the D, L, α, β, etc. The various stereoisomers as well as the racemic mixtures thereof are contemplated by the present invention. However, it is preferred that the compounds of the present invention are in the D-configuration.

Embodiments of the pharmaceutical compound according to the invention can molecularly be exemplified by the formulas for D-arabinitol-1,2,4-trisphosphate, D-glucose-2,5,6-trisphosphate and 1,5-anhydro-D-arabinitol-2,3,4-trisphosphate.

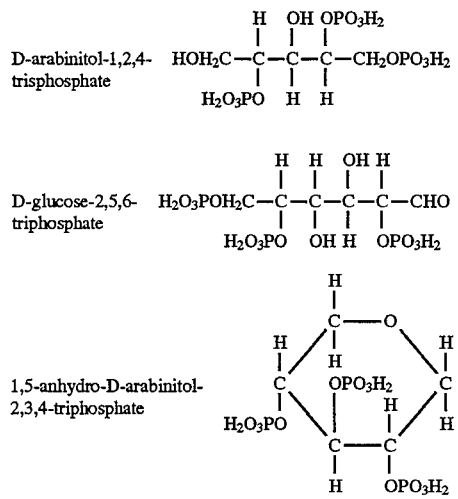

The pharmaceutically active ingredient is, in preferred embodiments of the present invention, selected from the group consisting of D/L-ribose trisphosphates, D/L-arabinose trisphosphates, D/L-xylose trisphosphates, D/L-lyxose trisphosphates, D/L-allose trisphosphates, D/L-altrose trisphosphates, D/L-glucose trisphosphates, D/L-mannose trisphosphates, D/L gulose trisphosphates, D/L-idose trisphosphates, D/L-galactose trisphosphates, D/L-talose trisphosphates, D/L-glucoheptose trisphosphates, D/L-mannoheptose trisphosphates, D/L-ribulose trisphosphates, D/L-xylulose trisphosphates, D/L-psicose trisphosphates, D/L-fructose trisphosphates, D/L-sorbose trisphosphates, D/L-tagatose trisphosphates and D/L-sedoheptulose or is selected from the group consisting of corresponding trisphosphorylated pentitols or anhydropentitols, hexitols or anhydrohexitols and heptitols or anhydroheptitols and/or salts thereof.

The preferred active ingredient of the present invention is the anhydropenitols, especially the 1,5-anhydropentitols, such as anhydroxylitol trisphosphate, and anhydroarabinitol trisphosphate.

The pharmaceutical composition can, in addition to the trisphosphorylated compound of the invention, also comprise other pharmaceutically active ingredients. In such cases the amount of additional active ingredient is 5%–95% and preferably 10%–95% by weight of the compound according to the invention.

It is suitable that the composition according to the invention exists in a unit dosage. Tablets, granules and capsules are suitable administration forms for such a unit dosage.

Tablets can be treated in different ways to protect the compound from uncontrolled hydrolysis in the stomach and/or intestine and/or to provide a desired absorption. Suitable administration forms include slow release formulation, transdermal formulations, nasal, rectal, intra-articular, intraperitoneal and subcutaneous administration. In some cases, it is preferable to use the unit dosage in the form of a solution for intravenous administration.

A unit dosage comprises 0.01–5.0 g, preferably 0.05–2.0 g and most preferably 0.10–2.0 g, of the pharmaceutically active ingredient.

The present invention also refers to a method of preventing or alleviating tissue damage, such as oedema formation and vascular leakage. Further conditions that can be treated with the pharmaceutically active ingredient according to the present invention are tissue damages caused by burns, rhinitis and asthma; bone disorders such as osteoporosis, Paget's disease, bone erosion and hypercalcemia; diabetes or complications thereof such as cataract formation, retinopathy, vascular complications, neuropathy, nephropathy, hyperglycemia and hyperketonemia; disorders related to transplantation and graft operations such as rejection; abnormal immunological reactions; abnormal levels of lipoproteins; cardiovascular diseases such as atherosclerosis; hypertension; thrombosis; hemorrhage; conditions of ischemia and reperfusion; conditions of shock; organ injury and damage to cells such as endothelial cells, platelets, and erythrocytes.

Conditions related to vasculitis, dermatitis, gastrointestinal diseases such as ulcerative colitis and pancreatitis, synovitis, periodontal diseases, cerebral diseases, eye diseases or damage to the retina or lens, light and oxygen induced diseases or damages, autoimmune diseases such as multiple sclerosis and metal intoxication are further conditions that the present pharmaceutical compositions are used to prevent, alleviate or combat. The method comprises administering to a mammal, including humans, a pharmaceutical composition consisting of at least one pharmaceutically active ingredient selected from the group consisting of trisphosphorylated pentoses, pentitols or anhydropentitols, trisphosphorylated hexoses, hexitols or anhydrohexitols and trisphosphorylated heptoses, heptitols or anhydroheptitols.

The pharmaceutical composition, in a preferred embodiment, is used in the form of tablets, granules, capsules or solutions. The appropriate dosages for administration to a human can routinely be determined by those skilled in the art by extension of results obtained from animal studies using various dosages. The preferred dosage falls within the range of 0.01 to 1000, preferably 0.05 to 600 and most preferably 0.1 to 200 mg/day and kg body weight.

The function of the pharmaceutical composition is to reverse, prevent or alleviate specific types of cell to cell attachment which are deleterious to the body. Cells with diverse functions, for instance granulocytes, neutrophils, etc., are activated under certain physiological or pathological conditions and adhere to other cell types such as endothelial cells. The adhesion process leads to different forms of cytotoxicity, phagocytosis, chemotaxis and induction of cell proliferation and differentiation. These events often lead to conditions described above such as tissue damage, cardiovascular diseases and other types of diseases.

A cell to cell adhesion process is regulated by specific types of receptors. Without wishing to be bound, it is believed that the mode of action of the pharmaceutically active ingredient of the invention, is to regulate the receptor function with primarily an antagonistic effect. The above mentioned process, furthermore, often involves cell damage and cell destruction caused by certain enzymes such as hydrolases, proteases and the like. Many of these enzymes, for example, lysosomal enzymes, are activated via processes involving receptor interactions.

In addition, the pharmaceutical composition of the present invention also interacts with these types of receptors with a beneficial regulation. It is believed that the pharmaceutically active ingredient of the invention acts via cytoprotection and stabilization of, for instance, cell membranes.

The stereochemical environment around $C_2$, $C_3$, $C_5$, and $C_6$ are essential for a proper reception interaction. $C_n$ is the number of different carbon atoms according to the valid nomenclature.

These and other objects and the attendant advantages will be more fully understood from the following detailed description, taken in conjunction with appended Examples 1–5, wherein: Examples 1 and 2 show preparation and characterization of pharmaceutically active compounds according to two embodiments of the present invention. The compounds are 1,5-anhydroxylitol-2,3,4-trisphosphate pentakis (cyclohexylammonium) salt and 1,5-anhydro-D-arabinitol-2,3,4-triphosphate pentakis (cyclohexylammonium) salt, respectively. Example 3 shows preparation of a solution of the compound of Example 1. The solution is intended for injections. Example 4 gives results from in vitro tests of the product obtained in Example 2—vascular leakage. Example 5 gives results from in vitro tests of 1,5-anhydro-D-arabinitol-2,3,4-trisphosphate—$IC_{50}$ values.

The following examples are given to illustrate the scope of the present invention. Because these examples are given for illustrative purposes, the invention should not be deemed limited thereto.

EXAMPLE 1

A stirred solution of 10.83 g of per-0-acetyl xylitol bromide in 30 ml of dry 1,2-dimethoxyethane was added dropwise to a stirred suspension of 13.0 g of lithium aluminum hydride in 200 ml of dry 1,2-dimethoxyethane kept under nitrogen at room temperature. After this processing, 3.34 g of 1,5-anhydroxylitol was obtained.

A stirred solution of 302 mg of the above obtained 1,5-anhyroxylitol in 3 ml of dry pyridine was treated for 30 minutes at 0° C. with 1.7 ml of diphenylchlorophosphate and thereafter kept at room temperature for 7 days. The mixture was treated with 0.5 ml of ice water and was after 10 minutes poured into 80 ml of an ice cold saturated aqueous solution of sodium hydrogen carbonate.

The mixture was thereafter stirred at room temperature for 2 hours. The mixture was extracted with 2×50 ml of dichloromethane and the combined extracts were washed successively with 2M hydrochloric acid, saturated aqueous sodium hydrogen carbonate and water and thereafter dried and concentrated in vacuo. Column chromatographic of the residue gave 1.27 g of 1,5-anhydroxylitol-2,3,4-tris (diphenylphosphate).

A solution of 623 mg. of this compound, i.e., 1,5-anhydroxylitol-2,3,4-tris (diphenylphosphate), in 30 ml of ethanol was treated with 100 mg of platinum oxide and the mixture was hydrogenated during 3 hours at room temperature. The supernatant was, after filtration, concentrated followed by addition of 0.53 ml cyclohexylamine. The resulting material, 848 mg. of 1,5-anhydroxylitol-2,3,4-trisphosphate pentakis (cyclohexylammonium) salt was recrystallized from a mixture of methanol and propanol.

The 1,5-anhydroxylitol-2,3,4-trisphosphate pentakis (cyclohexylammonium) salt exhibited the following P-NMR data: ($D_2O$): δ3.06, 1.62.

EXAMPLE 2

In an experiment similar to that of Example 2, 1,560 mg of 1,5-anhydro-D-arabinitol-2,3,4-trisphosphate pentakis (cyclohexylammonium) salt was obtained with the following P-NMR data: ($D_2O$): δ3.36, 3.09, 2.43.

EXAMPLE 3

500 mg of the 1,5-anhydroxylitol-2,3,4-trisphosphate pentakis (cyclohexylammonium) salt obtained in Example 1 was treated with a cation exchange resin in $H^+$ form followed by addition of 250 mg of NaOH and 770 mg of NaCl dissolved in 98.48 ml of water, to produce a solution suitable for injection into a mammal, including man.

EXAMPLE 4

A membrane preparation was obtained from rat brains in a way suitable to provide membrane fragments from plasma membranes. From earlier studies these membrane preparations are known to comprise binding sites for phosphorylated compounds. The physiological role of these binding sites are to regulate for example vascular leakage and oedema formation in the body. The degree of binding of a specific compound to these binding sites predicts the efficiency to counteract vascular leakage in vivo.

The membrane preparation was first saturated with a tritiated control compound. The control compound was D-myo-inositol-1,3,4,5-tetraphosphate ($IP_4$). Addition of a further compound having, increased binding properties, compared to the control compound, will result in a replacement of the control compound and thus in a reduction of the radioactivity in the sample.

The 1,5-anhydro-D-arabinitol-2,3,4-trisphosphate pentakis (cyclohexylammonium) salt obtained in Example 2 was added to a membrane preparation as described above. After washing, the radioactivity was 30% compared to the control compound ($IP_4$), thus showing a significant binding to the preparation. This result demonstrates a beneficial effect of 1,5-anhydro-D-arabinitol-2,3,4-trisphosphate pentakis (cyclohexylammonium) salt to reduce vascular leakage.

EXAMPLE 5

A membrane preparation for binding experiments was prepared at 4° C. Remaining blood was removed from fresh rats hearts (approx. 25 g) and the hearts were minced on chilled plates and blended thoroughly with 20 volumes (v/w) of 0.32M sucrose. The mixture was homogenized using a glass homogenizer followed by centrifugation at 800 g for 10 minutes. The supernatant was thereafter recentrifuged at 21000 g for 20 minutes. The resulting pellets were suspended in 20 volumes of ice cold water before homogenization and centrifugation. The supernatant was collected by pipetting followed by recentrifugation. The resulting pellets were homogenized in 20 volumes of 50 mM of Tris HCl (pH 7.7) and mixed with Triton X-100 to a final concentration of 0.04%. This mixture was incubated for 15 minutes at 37° C. and then centrifuged at 100,000 g for 10 minutes. The pellets were washed by homogenizing in 20 ml of 50 mM Tris HCl (pH 7.7). The final pellets were stored at −70° C. until further use.

The binding assays were performed in a final volume of 0.5 ml in microcentrifuge tubes. Membrane protein (0.12–0.18 mg), prepared as disclosed above, in 50 mM HEPES buffer (pH 7.4) was added to the tubes together with tritiated D-myo-inositol-1,2,6-triphosphate as a reference compound to a final concentration of 1 mM.

In order to determine the effect of a specific compound to replace the tritiated reference compound, appropriate concentrations of the investigated compound were added to different tubes.

The assay mixtures were incubated for 60 minutes in ice and binding reactions were terminated by centrifugation for 5 minutes. The surface of the pellets were washed with 1 ml of iced 50 mM HEPES buffer (pH 7.4) before measuring the incorporated radioactivity by means of a scintillation counter.

An $IC_{50}$ value can be determined by calculation of the replacement ratio of the tritiated reference compound at different concentrations of the specific compound. This value represents the concentration needed to replace half the amount of the tritiated reference compound and is expressed as log (conc. of compound). Thus a higher $IC_{50}$ value reflects a strong binding to the membrane preparation. Following the above described procedure the binding properties of 1,5-anhydro-D-arabinitol-2,3,4-trisphosphate was determined. The $IC_{50}$ value was −6.9.

Compounds having similar $IC_{50}$ values, such as D-myo-inositol-1,2,6-trisphosphate, have been shown to have significant anti-inflammatory and analgesic effects. Thus the obtained $IC_{50}$ value of −6.9 for 1,5-anhydro-D-arabinitol-2,3,4-trisphosphate predicates a strong anti-inflammatory and analgesic effect.

The above preferred embodiments and examples are given to illustrate the scope and spirit of the present invention. The embodiments and examples will make apparent, to those skilled in the art, other embodiments and examples. These other embodiments and examples are within the contemplation of the present invention. Therefore, the present invention should be limited only by the appended claims.

I claim:

1. A pharmaceutical composition comprising a pharmaceutically effective amount of a compound or pharmaceutically acceptable salt thereof in association with a pharmaceutically acceptable carrier, excipient or additive wherein said compound is:
   (a) a trisphosphorylated pentose,
   (b) a trisphosphorylated pentitol or a corresponding trisphosphorylated anhydropentitol,
   (c) a trisphosphorylated hexose,
   (d) a trisphosphorylated hexitol, or a corresponding trisphosphorylated anhydrohextitol,
   (e) a trisphosphorylated heptose, or
   (f) a trisphosphorylated heptitol or a corresponding trisphosphorylated anhydroheptitol.

2. The composition according to claim 1, wherein the pharmaceutically active compound is:
   (a) a D/L-ribose trisphosphate,
   (b) a D/L-arabinose trisphosphate,
   (c) a D/L-xylose trisphosphate,
   (d) a D/L-lyxose trisphosphate,
   (e) a D/L-allose trisphosphate,
   (f) a D/L-altrose trisphosphate,
   (g) a D/L-glucose trisphosphate,
   (h) a D/L-mannose trisphosphate,
   (i) a D/L-gulose trisphosphate,
   (j) a D/L-idose trisphosphate,
   (k) a D/L-galactose trisphosphate,
   (l) a D/L-talose trisphosphate,
   (m) a D/L-glucoheptose trisphosphate,
   (n) a D/L-mannoheptose trisphosphate,
   (o) a D/L-ribulose trisphosphate,
   (p) a D/L-xylulose trisphosphate,
   (q) a D/L-psicose trisphosphate,
   (r) a D/L-fructose trisphosphate,
   (s) a D/L-sorbose trisphosphate,
   (t) a D/L-tagatose trisphosphate, or
   (u) a D/L-sedoheptulose trisphosphate.

3. The composition according to claim 1, wherein the pharmaceutically active compound is:
   (a) a D/L-ribitol trisphosphate,
   (b) a D/L-arabinitol trisphosphate,
   (c) a D/L-xylitol trisphosphate,
   (d) a D/L-lyxitol trisphosphate,
   (e) a D/L-allitol trisphosphate,
   (f) a D/L-altritol trisphosphate,
   (g) a D/L-glucitol trisphosphate,
   (h) a D/L-mannitol trisphosphate,
   (i) a D/L-gulitol trisphosphate,
   (j) a D/L-iditol trisphosphate,
   (k) a D/L-galactitol trisphosphate,
   (l) a D/L-talitol trisphosphate,
   (m) a D/L-glucoheptitol trisphosphate,
   (n) a D/L-mannoheptitol trisphosphate,
   (o) a D/L-ribulitol trisphosphate,
   (p) a D/L-xylulitol trisphosphate,
   (q) a D/L-psicitol trisphosphate,
   (r) a D/L-fructitol trisphosphate,
   (s) a D/L-tagatitol trisphosphate, or
   (t) a D/L-sedoheptulitol trisphosphate.

4. The composition according to claim 1, wherein the pharmaceutically active compound is:
   (a) a D/L-anhydroribitol trisphosphate,
   (b) a D/L-anhydroarabinitol trisphosphate,
   (c) a D/L-anhydroxylitol trisphosphate,
   (d) a D/L-anhydrolyxitol trisphosphate,
   (e) a D/L-anhydroallitol trisphosphate,
   (f) a D/L-anhydroaltritol trisphosphate,
   (g) a D/L-anhydroglucitol trisphosphate,
   (h) a D/L-anhydromannitol trisphosphate,
   (i) a D/L-anhydrogulitol trisphosphate,
   (j) a D/L-anhydroiditol trisphosphate,
   (k) a D/L-anhydrogalactitol trisphosphate,
   (l) a D/L-anhydrotalitol trisphosphate,
   (m) a D/L-anhydroglucoheptitol trisphosphate,
   (n) a D/L-anhydromannoheptitol trisphosphate,
   (o) a D/L-anhydroribulitol trisphosphate,
   (p) a D/L-anhydroxylulitol trisphosphate,
   (q) a D/L-anhydropsicitol trisphosphate,
   (r) a D/L-anhydrofructitol trisphosphate,
   (s) a D/L-anhydrotagatitol trisphosphate, or
   (t) a D/L-anhydrosedoheptulitol trisphosphate.

5. The composition according to claim 1, wherein the pharmaceutically active compound 1,5-anhydroxylitol-2,3,4-trisphosphate.

6. The composition according to claim 1, wherein the pharmaceutically active compound is 1,5-anhydro-D-arabinitol-2,3,4-trisphosphate.

7. The composition according to claims 1, 2, 3, 4, 5 or 6 wherein the pharmaceutically active compound is present as a salt of sodium, potassium, calcium, magnesium or zinc.

8. The composition according to claims 1, 2, 3, 4, 5, or 6 wherein the pharmaceutically active compound is present as an ammonium salt.

9. The composition according to claim 1 wherein the pharmaceutical composition is a tablet, granule, capsule or solution.

10. The composition according to claim 9, wherein the unit dosage comprises 0.01 to 5.0 g of the pharmaceutically active compound.

11. The composition according to claim 9, wherein the unit dosage comprises 0.05 to 2.0 g of the pharmaceutically active compound.

12. The composition according to claim 9, wherein the unit dosage comprises 0.1 to 2.0 of the pharmaceutically active compound.

13. A method of preventing or alleviating tissue damage, the method comprising administering to a mammal a pharmaceutical composition comprising at least one pharmaceutically active ingredient selected from the group consisting of:
   (a) a trisphosphorylated pentose,
   (b) a trisphosphorylated pentitol or a corresponding anhydropentitol,
   (c) a trisphosphorylated hexose,
   (d) a trisphosphorylated hexitol or a corresponding anhydrohexitol,
   (e) a trisphosphorylated heptose, and
   (f) a trisphosphorylated heptitol or a corresponding anhydroheptitol, wherein said pharmaceutically active ingredient is administered in a dosage of 0.01 to 1000 mg/kg body weight per day.

14. The method according to claim 13, wherein said pharmaceutically active ingredient is present as a salt of sodium, potassium, calcium, magnesium or zinc.

15. The method according to claim 13, wherein said pharmaceutically active ingredient is present as an ammonium salt.

16. The method according to claims 13, 14 or 15, wherein said dosage is within a range of 0.05 to 600 mg/kg body weight per day.

17. The method according to claims 13, 14, or 15, wherein said dosage is within a range of 0.1 to 200 mg/kg body weight per day.

18. The method according to claim 13, wherein said tissue damage is an oedema.

19. The method according to claim 13, wherein said tissue damage is a vascular leakage.

\* \* \* \* \*

UNITED STATES PATENT AND TRADEMARK OFFICE
CERTIFICATE OF CORRECTION

PATENT NO. : 5,654,280
DATED : August 5, 1997
INVENTOR(S) : Matti Siren

It is certified that error appears in the above-indentified patent and that said Letters Patent is hereby corrected as shown below:

Column 2, line 6: "meals" should read --mammals--

Column 10, line 62, Claim 5: after "compound" insert --is--

Signed and Sealed this

Eighth Day of September, 1998

Attest:

BRUCE LEHMAN

*Attesting Officer*       *Commissioner of Patents and Trademarks*